(12) United States Patent
Vollrath

(10) Patent No.: US 7,803,144 B1
(45) Date of Patent: Sep. 28, 2010

(54) DEVICE FOR SUPPORTING AN EX-DWELLING CATHETER

(75) Inventor: Victor J. Vollrath, 7980 N. Pennsylvania St., Indianapolis, IN (US) 46240

(73) Assignee: Victor J. Vollrath, Indianapolis, IN (US)

( * ) Notice: Subject to any disclaimer, the term of this patent is extended or adjusted under 35 U.S.C. 154(b) by 0 days.

(21) Appl. No.: 12/480,189

(22) Filed: Jun. 8, 2009

(51) Int. Cl.
*A61F 5/44* (2006.01)
(52) U.S. Cl. .................. 604/349; 604/351; 604/353
(58) Field of Classification Search ......... 604/346–353; 2/78.2, 405
See application file for complete search history.

(56) References Cited

U.S. PATENT DOCUMENTS

| 3,161,198 | A | * | 12/1964 | Moxley | ............... 604/353 |
|---|---|---|---|---|---|
| 3,721,243 | A | * | 3/1973 | Hesterman et al. | ............ 604/67 |
| 4,568,340 | A | * | 2/1986 | Giacalone | ............... 604/353 |
| 4,713,066 | A | * | 12/1987 | Komis | ............... 604/353 |
| 5,158,556 | A | | 10/1992 | Starley | |
| 5,211,640 | A | | 5/1993 | Wendler | |
| 5,267,989 | A | | 12/1993 | Moyet-Ortiz | |
| 5,334,175 | A | | 8/1994 | Conway et al. | |
| 5,478,334 | A | | 12/1995 | Bernstein | |
| 5,752,944 | A | | 5/1998 | Dann et al. | |
| 5,897,540 | A | * | 4/1999 | Grundke et al. | ............... 604/352 |
| 6,113,582 | A | | 9/2000 | Dwork | |
| 6,248,096 | B1 | | 6/2001 | Dwork et al. | |
| 6,419,665 | B1 | | 7/2002 | Cohen | |
| 6,443,930 | B1 | | 9/2002 | Silverstein | |
| 6,565,545 | B1 | | 5/2003 | Frenche | |
| 6,565,546 | B1 | | 5/2003 | Hurst | |
| 6,635,037 | B1 | | 10/2003 | Bennett | |
| 6,635,038 | B2 | | 10/2003 | Scovel | |
| 6,679,867 | B2 | * | 1/2004 | Miskie | ............... 604/349 |
| 6,805,662 | B2 | | 10/2004 | Shah | |
| 6,904,914 | B2 | | 6/2005 | Badgett | |
| 7,018,366 | B2 | | 3/2006 | Easter | |
| 7,977,833 | | | 7/2006 | Bonham | |
| 7,125,399 | B2 | | 10/2006 | Miskie | |
| 7,143,768 | B2 | | 12/2006 | Miskie | |
| 7,160,276 | B2 | | 1/2007 | Bruns | |
| 7,166,092 | B2 | | 1/2007 | Elson et al. | |
| 2008/0243097 | A1 | * | 10/2008 | Goss | ............... 604/349 |

OTHER PUBLICATIONS

AlphaDry? The Basic System form AlphaDry Incontinent Men Dry and Free Again retrieved form http://alphadry.com/system.htm on Mar. 13, 2009.

* cited by examiner

*Primary Examiner*—Tatyana Zalukaeva
*Assistant Examiner*—Lynne Anderson
(74) *Attorney, Agent, or Firm*—Woodard, Emhardt, Moriarty, McNett & Henry, LLP

(57) ABSTRACT

A device for managing urinary incontinence in adult males includes an undergarment with a waistband and a front piece with a circular opening in it, a tubular support with a pair of spaced-apart flanges defining a groove that fits in the circular opening, and a condom catheter positioned in the tubular support by having the open end of the catheter fit around one end of the tubular support member, and by having the sheath portion of the condom catheter extend through and be supported by the tubular support.

4 Claims, 5 Drawing Sheets

DEVICE FOR SUPPORTING AN EX-DWELLING CATHETER

FIELD OF THE INVENTION

The present invention relates generally to devices for holding and supporting an ex-dwelling catheter, and more particularly to a device for holding and supporting an ex-dwelling condom catheter such as may be worn by incontinent men.

BACKGROUND TO THE INVENTION

Male urinary incontinence is the accidental release of urine. It may be caused by prostate problems; head and/or spinal cord injury; neurological or degenerative diseases; urinary tract infection; the aging process; toxins, including too much alcohol; medications; and emotional distress.

Among the treatments that may be effective for treating male incontinence are: medicines, exercises, surgery, and lifestyle changes that may alleviate the problem. When these treatments cannot be used or are ineffective, there are products available to assist men in dealing with incontinence issues. One such product is the condom catheter, a sheath-like device that is worn like a condom and includes a reservoir for receiving and storing urine. The AlphaDry system, made by AlphaDry Medical LLC, Salem, Oreg., is one such condom catheter.

The AlphaDry condom catheter is a combination one-piece condom catheter, one-way valve, and reservoir that tucks into a person's brief-style underwear. The device looks like a large, baggy condom with a somewhat bulbous end. The device is used by first rolling down the upper portion of the condom until the internal valves of the device are exposed. The device is then positioned at the head of the penis, and the rolled upper end of the device is unrolled onto the penis as a condom would be. A securing strap is tightened around the base of the penis to hold the device in place, and the penis and device are tucked in the underwear. When the person's urine is released, the urine flows through the one-way valve into the reservoir. The device is emptied periodically, and is cleaned at least daily.

One problem that has been recognized by men using the AlphaDry condom catheter is that it is uncomfortable to wear. Even when the securing band is firmly attached, the device can sag and pull uncomfortably on the penis.

It can be seen from the above that a need exists for a device for holding and supporting an ex-dwelling condom catheter such as an AlphaDry condom catheter. The present invention addresses that need.

SUMMARY OF THE INVENTION

In one aspect of the present invention there is provided a device for managing urinary incontinence in adult males. In one embodiment the device comprises:

a) an undergarment having a waistband and a front piece, with a substantially circular opening in said front piece of said undergarment, wherein said substantially circular opening is sized to receive an open end of a condom catheter;

b) a tubular support member removably received in said substantially circular opening, wherein said tubular support member has a first end and a second end, wherein said first end includes a pair of spaced-apart flanges defining a undergarment-receiving groove sized to be received in said substantially circular opening and effective for retaining the tubular support member therein, and wherein said tubular support member includes a catheter-receiving groove sized to receive the open end of a condom catheter; and c) a condom catheter partially disposed in and supported by said tubular support member, wherein said condom catheter has a sheath portion terminating in an open end and a reservoir portion terminating in a closed end, wherein said condom catheter is partially disposed in and supported by the tubular support member by having the open end of the catheter positioned in the catheter-receiving groove of the tubular support member, and by having the sheath portion of the condom catheter extend through and be supported by the tubular support member.

In another embodiment the device comprises:

a) an undergarment having a waistband and a front piece, with a substantially circular opening in said front piece of said undergarment, and further with a support ring affixed in said front piece opening, wherein said support ring is sized to receive and connect to a condom catheter;

b) a condom catheter releasably connected to said support ring, wherein said condom catheter has a sheath portion terminating in an open end and a reservoir portion terminating in a closed end, wherein the sheath portion of said condom catheter is releasably connected to the support ring.

In a third embodiment the device comprises an undergarment having a waistband and a front piece, with a substantially circular opening in said front piece of said undergarment, and further with a support ring affixed in the front piece opening, wherein the support ring is sized to receive and connect to a condom catheter.

The inventive device improves the safety and comfort of prior art catheter systems, and may be referred to as a "Safeguard Exdwelling Catheter" system.

DESCRIPTION OF THE PREFERRED EMBODIMENTS

For the purposes of promoting an understanding of the principles of the invention, reference will now be made to certain embodiments and specific language will be used to describe the same. It will nevertheless be understood that no limitation of the scope of the application is thereby intended. Instead, the claims of the application are intended to cover all alterations and further modifications in the illustrated invention, and such further applications of the principles of the invention disclosed herein, as would normally occur to one skilled in the art to which the invention relates.

One aspect of the present invention provides a device for managing urinary incontinence in adult males. In one embodiment the device comprises:

a) an undergarment having a waistband and a front piece, with a substantially circular opening in said front piece of said undergarment, wherein said substantially circular opening is sized to receive an open end of a condom catheter;

b) a tubular support member removably received in said substantially circular opening, wherein said tubular support member has a first end and a second end, wherein said first end includes a pair of spaced-apart flanges defining a undergarment-receiving groove sized to be received in said substantially circular opening and effective for retaining the tubular support member therein, and wherein said tubular support member includes a catheter-receiving groove sized to receive the open end of a condom catheter; and c) a condom catheter partially disposed in and supported by said tubular support member, wherein said condom catheter has a sheath portion terminating in an open end and a reservoir portion terminating in a closed end, wherein said condom catheter is partially disposed in and supported by the tubular support member by having the open end of the catheter positioned in the catheter-receiving groove of the tubular support member, and by having the sheath portion of the condom catheter extend through and be supported by the tubular support member.

Figure 1:
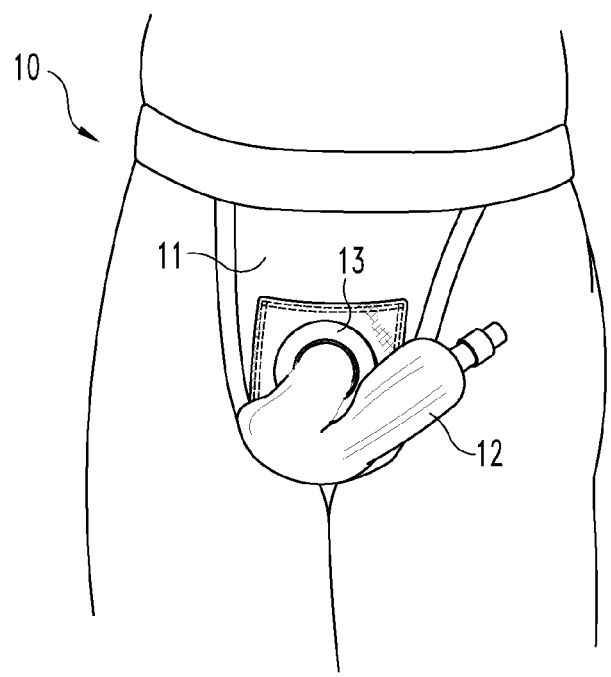
FIG. 1 shows the device of the present invention as worn by a person, according to one preferred embodiment.

Referring to the drawings, FIG. 1 shows the device of the present invention as worn by a person, according to one preferred embodiment. Device 10 includes undergarment 11 with tubular support member 13 supporting condom catheter 12.

Figure 2:
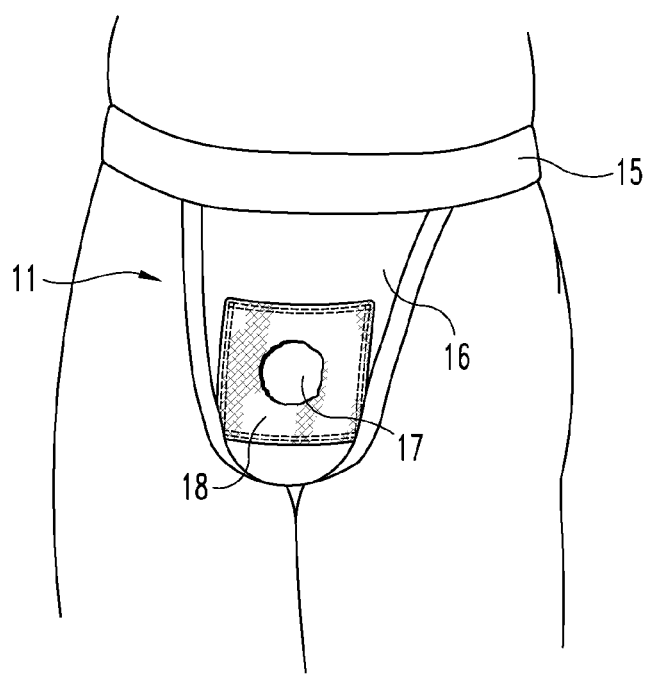
FIG. 2 shows undergarment portion of the device of the present invention, according to one preferred embodiment.

FIG. 2 shows undergarment portion of the device of the present invention, according to one preferred embodiment. Undergarment 11 includes waistband 15 and front piece 16. An opening 17 is provided in front piece 11 to receive a tubular support member. Opening 17 is sized to receive a condom catheter supported by a tubular support member, and is accordingly preferably between about 1.25" and 2.25" in diameter, with a diameter of about 1.75" being most preferred in testing to date. Opening 17 may be reinforced by reinforcing material 18 around the opening. The reinforcing material helps maintain a proper opening size and lends support and stability to the opening.

Figure 3:
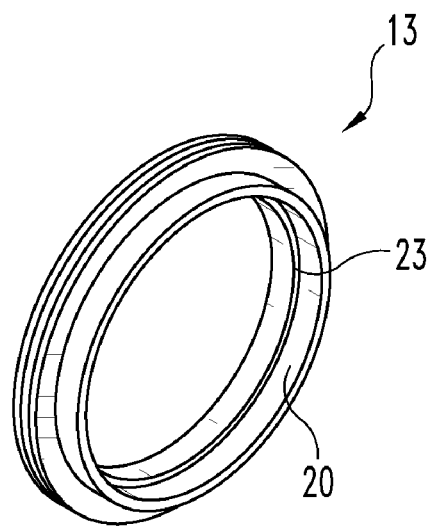
FIG. 3 shows the support ring portion of the device of the present invention, according to one preferred embodiment.
Figure 4:
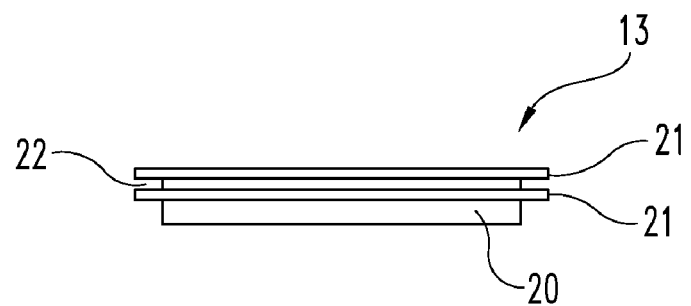
FIG. 4 is another view of the support ring portion of the device of the present invention, according to one preferred embodiment.

FIGS. 3 and 4 show the support ring portion of the device of the present invention, according to one preferred embodiment. Support ring 13 includes a body 20 with a pair or opposing flanges or rims 21 at one end. The pair of opposing flanges 21 defines an undergarment-receiving groove 22. A lip 23 may be provided to assist positioning a support tube in the support ring.

Figure 5:
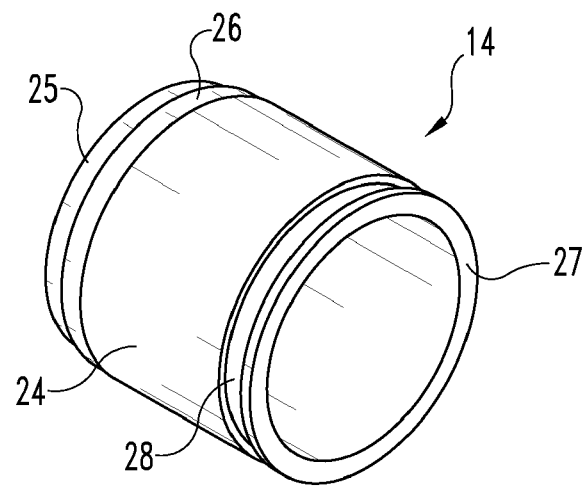
FIG. 5 shows the support tube portion of the device of the present invention, according to one preferred embodiment.
Figure 6:
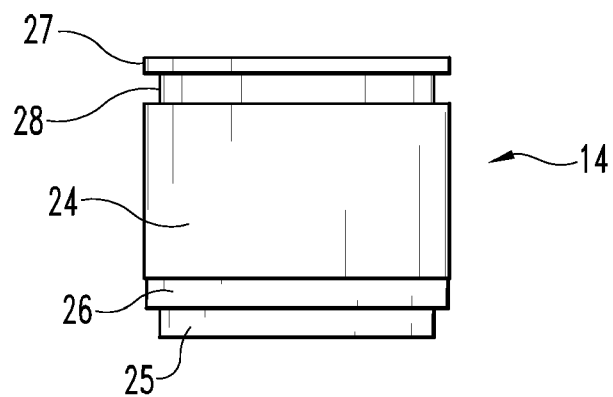
FIG. 6 is another view of the support tube portion of the device of the present invention, according to one preferred embodiment.

FIGS. 5 and 6 show the support tube portion of the device of the present invention, according to one preferred embodiment. Support tube 14 includes a body 24 ending in an inner end 25 and a rim end 27. A catheter-receiving groove 28 is defined by a reduced diameter portion of the support tube body adjacent rim end 27. In one preferred embodiment inner end 25 has a reduced diameter when compared to the main portion of support tube 24 so that inner end 25 fits in support ring 13. A second portion of support tube 14 may have a diameter that is slightly larger than inner end 25, but slightly smaller than the main body portion 24, to define a ridge 26 that facilitates securing support tube 14 in support ring 13. Support ridge 26 may rest on support ring lip 23 when support tube 14 is snapped into support ring 13.

Figure 7:
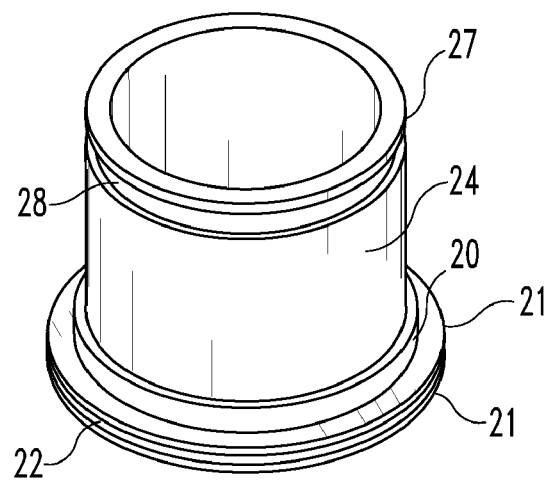
FIG. 7 shows the tubular support member of the present invention, according to one preferred embodiment.

FIG. 7 shows the tubular support member of the present invention, according to one preferred embodiment. Support tube 14 has been positioned in support tube 13 so that undergarment-receiving groove 22 is at one end of the tubular support member and catheter-receiving groove 28 is at the other end of the tubular support member. Support tube body 24 extends from support ring 13, with support body inner end 25 and support body ridge 26 being within support ring 13.

Figure 8:
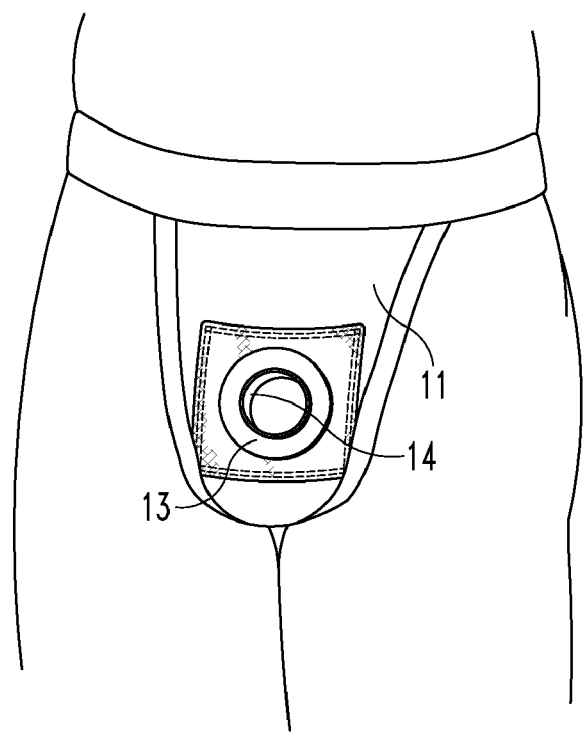
FIG. 8 shows the undergarment and tubular support member of the present invention when worn by a person, according to one preferred embodiment.

FIG. 8 shows the undergarment and tubular support member of the present invention when worn by a person, according to one preferred embodiment. Undergarment 11 holds support ring 13, which holds support tube 14.

Figure 9:
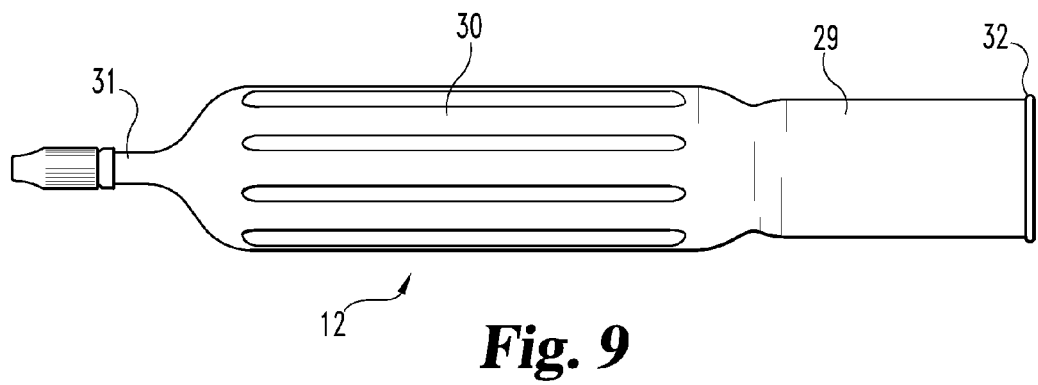
FIG. 9 shows a condom catheter that may be used in the present invention.

FIG. 9 shows a condom catheter that may be used in the present invention. Condom catheter 12 includes a sheath portion 29 terminating in rolled end 32, and a reservoir portion (alternatively referred to as a bladder portion) 30 terminating in catheter tip 31.

Figure 10:
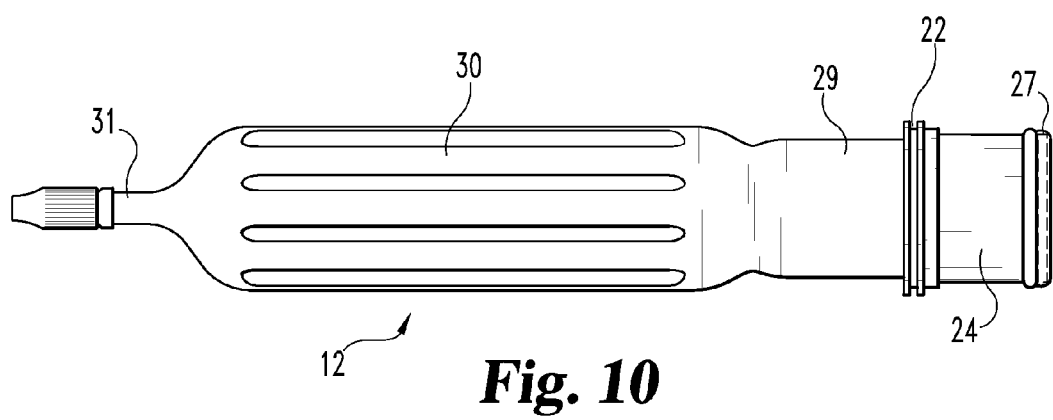
FIG. 10 shows a condom catheter attached to the support tube of the present invention, according to one preferred embodiment.

FIG. 10 shows a condom catheter attached to the support tube of the present invention, according to one preferred embodiment. Condom catheter sheath portion 29 is inserted in support tube body 24 with rolled end 32 sticking out of one end and reservoir 30 protruding from the other end of the tube body. Condom catheter rolled end 32 is pulled back over support body rim end 27 so that sheath portion 20 or rolled end 32 rests in catheter-receiving groove 28. In the illustrated embodiment rolled end 32 rests in catheter-receiving groove 28, but in an alternative embodiment a lower portion of sheath 29 may be positioned in groove 28. A rubber band may be used to firmly secure sheath 29 or rolled end 32 in catheter-receiving groove 28.

As to the method of use, the device is preferably assembled by positioning support ring 13 in opening 17 of undergarment 11. Support tube 14 may then be positioned in support ring 13 so that support ring 13 and support tube 14 form a tubular support member.

In some embodiments support ring 13 and support tube 14 are separate pieces as illustrated herein, although in other embodiments the tubular support member is made of a single piece that functions as a support ring and a support tube. Regardless of whether a two-piece construction or a unitary construction is used, the support ring may be removable from the undergarment or it may be sewn in place.

A condom catheter is placed on the tubular support member by inserting condom catheter sheath portion 29 into support tube body 24 so that rolled end 32 extends out of one end and reservoir 30 extends out of the other end of the tube body. Rolled end 32 is then pulled back over support body rim end 27 so that rolled end 32 either passes or rests in catheter-receiving groove 28, as described above. If rolled end 32 passes catheter-receiving groove 28, a rubber band may be used if desired to hold sheath portion 29 firmly in catheter-receiving groove 28. Alternatively, the rolled end itself may be secured in catheter-receiving groove 28.

The undergarment is worn by a male in need of protection against the accidental release of urine. The penis is placed in the sheath of the condom catheter so that urine will flow into the reservoir. The bladder portion of the device is preferably left in a hanging position, such as down along the left leg. The device supports the catheter without stressing or irritating the penis.

As to the particulars of the various components, the condom catheter may be any condom catheter such as the AlphaDry catheter that is illustrated in the drawings. That system, made by AlphaDry Medical LLC, Salem, Oreg., provides a one-piece condom catheter with a one-way valve and a reservoir that tucks neatly into a person's underwear for additional support. The urine flows directly through the one-way valve into the reservoir is periodically emptied. The AlphaDry catheter is made of latex, although other materials may be used.

The tubular support member may be a one-piece or a multi-piece construction that preferably has the following features: 1) it preferably provides a mechanism for removably attaching to an undergarment (although is some embodiments the tubular support member is "permanently" attached to the undergarment); 2) it preferably provides a support tube body to securely hold the condom catheter and support at least part of the penis therein; and 3) it preferably provides a mechanism for removably attaching a condom catheter to the tubular support member so that the condom catheter may be supported when in use, but removed for cleaning, etc.

As mentioned above, the tubular support member may be removably or permanently affixed to the undergarment. To accomplish that, an undergarment-receiving groove may be used, as herein described. Alternatively, the tubular support member may be sewn into the undergarment, or may be attached to the undergarment using other methods of temporary or more "permanent" attachment. The choice of temporary or more permanent attachment applies regardless of whether the tubular support member is a one-piece or a multi-piece construction, although it is understood that when the tubular support member is a multi piece construction it is possible that only one or the pieces is attached to the undergarment.

In one preferred embodiment the tubular support member has a tube body that is about 1.5" to 2" long and about 1.5" to 2" in diameter. The most preferred dimensions are about 1.75" long and 1.75" in diameter. In another embodiment the tubular support member has a length of about ½" to 1". In this "shortened" embodiment the support member is preferably made of a single piece that provides a support ring and little, if any, support tube.

The tubular support may be made of a material that is strong enough to provide structural support and resist deformation, but also comfortable to wear. The tubular support should be made of a material that is easy to clean. When the tubular support member is made of a two-piece construction such as is illustrated by the drawings herein, the support ring and the support tube may be made of the same material, or they may be made of different materials. Further, when the device is made with a multi-piece tubular support member, the pieces may fit together by press-fit, snap-fit, threaded portions, or other temporary or permanent methods of connection.

It is to be appreciated that one advantage of the inventive device is that the condom catheter is connected to and supported by the tubular support member rather than directly by the person's penis. This allows greater pressure to be used to secure the "open" end of the catheter, without that pressure being applied to the penis. Improved comfort and sealing of the open end results.

It is also to be appreciated that the tubular support member may be made in substantially any length desired. Longer support tubes may be used when it is desired to provide greater support to the penis, while shorter support tubes may be used if less support is desired. In some embodiments the tubular support member consists essentially of a support ring that is secured or securable to the undergarment, yet provides a structure for attachment of the catheter.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A device for managing urinary incontinence in adult males, comprising:
    a) an undergarment having a waistband and a front piece, with a substantially circular opening in said front piece, wherein said substantially circular opening is sized to removably receive a tubular support member;
    b) a tubular support member removably received in said substantially circular opening, wherein said tubular support member has a first end and a second end and an inner surface and an outer surface, wherein said first end includes a pair of spaced-apart flanges defining a undergarment-receiving groove sized to be received in said substantially circular opening and effective for removably retaining the tubular support member therein, and wherein said second end extends inward from said undergarment and includes a catheter-receiving groove in its outer surface to receive the rolled, open end of a condom catheter; and
    c) a condom catheter partially disposed in and supported by said tubular support member, wherein said condom catheter has a sheath portion terminating in a rolled, open end and a reservoir portion, wherein said condom catheter extends completely through and is supported by the tubular support member, and wherein the rolled end of the condom catheter is received in the catheter-receiving groove of the tubular support member.

2. The device of claim 1 wherein said tubular support member comprises a support tube removably connected to a support ring.

3. A device according to claim 1 wherein said substantially rigid tubular support member has a length of between about 1.5 inches and about 2.0 inches.

4. A device according to claim 1 wherein said device further includes a rubber band overlaying and securing the rolled end of said condom catheter in said catheter-receiving groove.

* * * * *